United States Patent [19]

McConnell

[11] 4,057,669
[45] Nov. 8, 1977

[54] METHOD OF MANUFACTURING A DRY-FORMED, ADHESIVELY BONDED, NONWOVEN FIBROUS SHEET AND THE SHEET FORMED THEREBY

[75] Inventor: Albert L. McConnell, Wallingford, Pa.

[73] Assignee: Scott Paper Company, Philadelphia, Pa.

[21] Appl. No.: 558,134

[22] Filed: Mar. 13, 1975

[51] Int. Cl.² .......................................... B29D 27/00
[52] U.S. Cl. ................................. 428/152; 264/118;
264/128; 264/134; 264/283; 428/153
[58] Field of Search ............... 264/134, 283, 118, 128;
428/152, 153

[56] References Cited

U.S. PATENT DOCUMENTS

| | | | |
|---|---|---|---|
| 2,545,952 | 3/1951 | Goldman | 154/46 |
| 2,865,783 | 12/1958 | Henderson | 117/5.5 |
| 3,295,526 | 1/1967 | Sabee | 128/287 |
| 3,485,695 | 12/1969 | Ness | 156/229 |
| 3,665,921 | 5/1972 | Stumpf | 128/287 |
| 3,879,257 | 4/1975 | Gentile et al. | 264/283 X |
| 3,903,342 | 9/1975 | Roberts | 428/153 |

Primary Examiner—Richard R. Kucia
Attorney, Agent, or Firm—Martin L. Faigus; William J. Foley

[57] ABSTRACT

A method of manufacturing a dry-formed, adhesively bonded, nonwoven fibrous sheet and the fibrous sheet formed thereby. The method includes the steps of forming a low integrity fibrous web by a dry-forming process; temporarily stabilizing the web with substantially brittle bonds for imparting desired properties to the completed sheet resulting from the subsequent processing operations; applying to a surface of the temporarily bonded web a permanent binder which penetrates at least about 10% through the thickness of the web, and which is in a spaced-apart pattern occupying from about 10 to about 60% of the surface area of the web; adhering to a creping surface, by use of the permanent binder, the areas of the web surface on which the permanent binder has been disposed; creping the web from the creping surface to break the brittle, temporary bonds for enhancing the bulk, flexibility, extensibility and porosity of the web; and drying and setting the permanent binder to complete the formation of the fibrous sheet of this invention.

24 Claims, 4 Drawing Figures

4,057,669

METHOD OF MANUFACTURING A DRY-FORMED, ADHESIVELY BONDED, NONWOVEN FIBROUS SHEET AND THE SHEET FORMED THEREBY

BACKGROUND OF THE INVENTION

1. Field of the Invention

This invention relates generally to a unique method for manufacturing a dry-formed, adhesively bonded, nonwoven fibrous sheet and to the sheet formed thereby. Specifically, this invention relates to a unique method for manufacturing a dry formed, adhesively bonded and creped nonwoven fibrous sheet having a high degree of bulk, flexibility, extensibility and porosity so as to permit the sheet of this invention to be used as a substitute for other nonwoven materials and conventional textile materials in absorbent products.

2. Description of the Prior Art

Dry-formed, nonwoven fibrous sheets have become exceedingly popular, especially for single or limited use applications, to replace higher cost textile webs formed by conventional textile operations, such as by weaving and knitting. Obviously, it is highly desirable to form the nonwoven sheets in a manner which will impart properties thereto that are similar to those possessed by the conventional textile fabrics which they are intended to replace. Specifically, it is desired to form such nonwoven sheets in a manner to impart sufficient bulk, flexibility and extensibility thereto for approximating the "hand" of such textile fabrics. Also, for many applications the nonwoven sheets should be absorbent and/or porous. Absorbent and/or porous nonwoven sheets are commonly employed as replacements for conventional textile fabrics as household and industrial wipers, as well as cover sheets for sanitary napkins and disposable diapers.

The initial step in the formation of dry-formed, nonwoven fibrous sheets is to form a dry fibrous web having a low integrity. It is often difficult to sustain the integrity of this web as it is directed through subsequent processing operations, such as, gravure printing operations and various post-treating operations, i.e., embossing, compacting, winding and the like.

To overcome the processing problems associated with the handling of low integrity, dry formed webs, it has been suggested in the prior art to initially strengthen the web by the inclusion of pre-bonding material, which may be either of a temporary type, or of a permanent type, for permitting the subsequent post-treating operations to be carried out without web failure. In these prior art methods, either the type and/or amount of the pre-bonding material is chosen to avoid any negative effect on the desired properties in the completed sheet (e.g., stretch, flexibility, absorbency, etc.), or, if the type of bonding material does adversely affect the properties of the completed sheet, it is washed out.

U.S. Pat. No. 3,676,245, issued to Helmut et al., discloses the temporary strengthening of a continuous filament web, prior to the final bonding thereof, by directing fine droplets of water onto the web surface. The surface tension of the water temporarily strengthens the freshly formed web so that it can be directed through the subsequent processing operations of adding a binder to the web and heating and drying the web for hardening or setting of the binder. Upon drying of the web the water which was initially applied to temporarily strengthen it will have been dissipated, and therefore will not provide any negative effect on the properties associated with the completed sheet.

In U.S. Pat. No. 2,719,802, issued to Nottebohm, a prebinder, in the form of a resin foam, is applied to a web surface to provide light surface cohesion prior to adding additional binder to the web to complete its structure. The bonding materials suggested for use in the Nottebohm patent are not of the type which form brittle bonds, and therefore may not adversely affect the flexibility, softness and drape of the completed sheet, unless an excess quantity of adhesive is applied.

In U.S. Pat. No. 3,485,695, issued to Ness, both the pre-bonding material and the final bonding material are elastomeric, and both create permanent bonds in the completed web. These binder materials are chosen so as not to adversely affect the formation of a web having textile-like properties, i.e., flexibility, softness and drape.

It is known to employ temporary binders of the type contemplated for use in this invention, to temporarily bond a dry-formed web so that said web can be further processed, as evidenced by the disclosures in U.S. Pat. Nos. 2,865,783, issued to Henderson et al. and 2,545,952, issued to Goldman.

Henderson et al. disclose washing out the brittle, temporary bonds between fibers by passing the web through a hot water bath after said web has been completely formed. The addition of water to the completed web is undesirable since additional drying equipment is required to remove the water, and this adds to the cost and complexity of the manufacturing process.

Goldman discloses a spot bonded, dry-formed web, and indicates that for some applications a small amount of starch can be added to facilitate the processing of the web. Goldman indicates that the inclusion of small amounts of starch is not inconsistent with the formation of a flexible web so long as the web is capable of flexing. However, a dry-formed sheet including brittle starch bonds therein does provide some degree of stiffness, as well as an undesirable hand in the completed sheet.

Print bonded fibrous webs of general interest to the subject matter of the instant invention are disclosed in U.S. Pat. Nos. 2,705,498, issued to Johnson; 2,958,608, issued to Barnard; 3,059,313, issued to Harmon; 3,236,718, issued to Cohen et al.; 3,665,921, issued to Stumpf; 3,665,922, issued to Skora and British Pat. No. 1,294,794, assigned to Scott Paper Company. In all of these patents, with the exception of the Johnson patent, a bonded fibrous web is mechanically worked as part of the formation process. However, none of these patents are concerned with, nor suggest a solution to the problem of low web integrity associated with a dry-forming operation, such as an air-laying, carding, garnetting or similar operation.

SUMMARY OF THE INVENTION

This invention resides in a unique method for manufacturing a dry-formed, adhesively bonded nonwoven sheet which is bulky, flexible, extensible and porous. A nonwoven sheet having a combination of the above properties also forms a part of this invention. Such a nonwoven sheet closely approximates the hand and appearance of textile fabrics manufactured by conventional textile operations, e.g., weaving and knitting.

The method of this invention is markedly different from the earlier discussed prior art methods of manufacturing dry-formed, adhesively bonded fibrous sheets. Specifically, the instant invention employs brittle bonds to temporarily stabilize a low integrity, dry-formed nonwoven web, and then takes advantage of the properties of the brittle bonds in the subsequent processing operations to aid in achieving the formation of a bulky, flexible, extensible and porous nonwoven sheet.

The development of brittle bonds in a nonwoven sheet has generally been brought to be inconsistent with an objective of achieving textile-like properties in said sheet. Specifically, Goldman (U.S. Pat. No. 2,545,952) indicates that the quantity of starch which is added should be small so as not to adversely affect product properties. Goldman does not rely upon the inclusion of starch to impart any desirable properties to his completed web. Henderson et al. (U.S. Pat. No. 2,865,783) clearly teach washing out a temporary brittle bonds from a nonwoven sheet after the sheet has been completely formed to thereby eliminate the stiffness which the bonds would otherwise impart to said sheet.

Specifically, the method of the instant invention includes the steps of initially dry-forming a fibrous web having a relatively low integrity; bonding the low integrity web with a binder which establishes brittle bonds for temporarily stabilizing the web so that it will have sufficient integrity for the subsequent processing operations; thereafter, applying a permanent binder to a surface of the temporarily bonded web so that, prior to creping, it penetrates at least 10% through the thickness of the web and is in a spaced-apart pattern covering from about 5 to 60% of the surface area of the web; adhering to a creping surface, by use of the permanent binder, the areas of the web surface in which the permanent binder has been disposed; creping the web from the creping surface for breaking the brittle bonds; and drying and setting the permanent binder to complete the formation of the dry-formed, nonwoven sheet of this invention.

The temporary brittle bonds between fibers in the web initially resist the compressive action imposed upon the web during the creping operation. However, when the force exceeds the compressive loading which can be tolerated at the temporary brittle bonds it is believed that the temporary bonds, in regions of the web which are free of permanent binder, will rupture in a relatively explosive manner. Accordingly, the web regions which are free of permanent binder will become puffed-up to enhance the bulk and porosity of said web regions. moreover, since the brittle bonds are broken during the creping operation the brittleness and poor hand of the web, prior to creping, will be eliminated. From the above, it can be seen that according to this invention, the brittle property of the bonds is actually taken advantage of in the process without imparting a harsh hand to the completed sheet.

The drying and setting of the permanent binder can be achieved in any desired manner. For example, the web can be dried on the creping surface, and the setting of the adhesive can take place in a subsequent operation, either by a heating or a cooling operation, depending upon the type of permanent binder which is employed. Alternatively, both the drying and the setting of the adhesive can be achieved on the creping surface. The manner in which the drying and setting of the permanent binder is carried out is not to be considered to be critical to this invention; however, the binder must have a sufficient affinity for a creping surface to permit adherence of the web to the creping surface through the permanent binder at the location in which said web is creped from said surface.

The method of this invention can be employed to form nonwoven sheets including various types of fibers therein. For example, the fiber content can range from 100% short cellulosic fibers of a paper making length less than ¼ inch (e.g., wood pulp and cotton linters) to 100% textile-length fibers having an average fiber length greater than ¼ inch, and generally up to about 2½ to 3 inches in length. Suitable long fibers for use in this invention can be either natural or man-made. Examples of suitable long fibers which can be employed in this invention are cotton, rayon, polyolefin, polyester, acetate, acrylic, polyamide and other materials. The particular long fiber employed in this invention is not considered to be critical. Generally, the particular long fiber employed in the method and article of this invention will be predicated upon availability, cost and the properties desired in the completed nonwoven sheet.

The temporary binder, when employed in the formation of a dry-formed web in accordance with the method of this invention, must be capable of: (1) forming fragile bonds between fibers, which bonds are sufficiently brittle to be broken during a subsequent creping operation; and (2) forming fragile bonds which, when the temporarily bonded web is dry, provide the requisite strength to the web to permit said web to be carried under tension through subsequent processing steps, which steps may include the bonding of the web with a permanent binder and the creping of the web off of a creping surface. In order to provide the requisite strength to the web, the temporary binder must either have a relatively high degree of polymerization (DP), or be capable of developing a high DP in the web. The DP is the number of recurring units in the polymer chain, and must be sufficiently high to provide a binder which imparts the necessary strength to the web to permit said web to be subsequently processed. Preferably, the DP is at least 1,000, and more preferably over 10,000. An optional property of the temporary binder is that it be water-rewettable, i.e., hydrophilic. This property is desirable when the nonwoven sheet is to be employed as an absorbent product.

Many different materials, either natural or synthetic, can be employed as the temporary binder in this invention. Examples of natural bonding agents are animal glue, casein, gums, starch, and starch modification such as dextrin. Examples of synthetic bonding materials are carboxymethylcellulose, urea-formaldehyde resin, polyvinyl alcohol and its acetate copolymers, polyacrylic acid and polyacrylamides. One of the most desirable temporary binders for use in this invention is starch because it is inexpensive and readily available.

The temporary binder is preferably uniformly and continuously disposed over the planar extent of the web, and preferably completely penetrates through the thickness of said web. The temporary binder preferably constitutes less than 10% of the fiber weight of the web, and more preferably is in the range of from about 2 to about 5% of the fiber weight of the web.

The temporary binder can be applied immediately after web formation by being sprayed, padded, coated, etc. onto one or both surfaces of the web in a manner that does not adversely affect web integrity. Alternatively, the temporary binder, in powder form, can be mixed with the fibers during initial web formation, and small quantities of moisture can be added to initiate the temporary bonding action. The web containing the temporary bonding material is then dried, such as by directing hot air through the web or passing the web over a series of dryer cans, to effect bonding of the web by the temporary binder. Preferably, the web is lightly calendered either prior to, or during drying to bring the fibers into sufficiently close association with each other to permit the temporary bonding mechanism to take place. This is particularly important when starch, or other similar hydrogen bonding material is employed. The stiff, brittle bonds imparted to the web by the temporary binder establishes sufficient integrity to the web to permit it to be conveyed through the subsequent processing steps, and in addition, to prevent fiber picking on print bonding rolls which may be employed to add the permanent binder in a spaced-apart pattern to the web.

The permanent binder employed in the invention must be capable of: (1) bonding the fibers to one another in the completely formed creped, nonwoven sheet; and (2) adhering the web to a creping surface at the time it is creped therefrom. In general, any material having these two capabilities may be utilized as the permanent bonding material if the material can be dried or cured to set it. Examples of permanent bonding materials which are capable of accomplishing both of the above functions, and which can be successfully utilized in this invention are polymeric emulsions or dispersions of ethylene, vinyl acetate, acrylic, styrene, butadiene, vinyl chloride, vinylidine chloride, and copolymers of the above with or without internal cross-linking sites. Preferably, the permanent binders employed in this invention are more flexible than the temporary binders.

The permanent binder is applied to the nonwoven web in a spaced-apart pattern which, preferably, is a predetermined pattern that can be varied as desired. For example, any of the patterns disclosed in U.S. Pat. Nos. 3,047,444; 3,009,822; 3,059,313 and 3,009,823 may be advantageously employed in this invention. The preferred pattern is reticular in which the permanently bonded areas are interconnected to form a net-like bonded network over the surface of the web. This pattern is preferred because stabilization of the web can be achieved with a greater spacing between binder areas, as compared to discrete binder patterns such as lines, bars and dots. In this manner, the porosity of the web is enhanced.

Depending upon the basis weight of the nonwoven sheet which is to be formed, the permanent binder can be applied to one or both major surfaces of the nonwoven fibrous web. However, in all embodiments of this invention, the permanent binder is applied to at least one of the surfaces in a spaced-apart pattern, and at least a web surface containing are spaced-apart pattern of permanent binder thereon is creped. If desired, both major surfaces can include a spaced-apart pattern of permanent binder, and each surface can be creped from a creping surface in accordance with the preferred method disclosed in copending U.S. application Ser. No. 356,052, filed on Apr. 30, 1973 now U.S. Pat. No. 3,879,257, issued Apr. 22, 1975 and assigned to Scott Paper Company.

Preferably, the permanent binder is present in the nonwoven sheets in a solids weight of from about 5 to about 30% of the fiber weight of the sheet. The actual concentration of permanent binder in the spaced-apart, print bonded areas is, in all cases, greater than the concentration of the temporary binder in the web regions which are free of permanent binder.

The nonwoven sheets of this invention formed according to the method of this invention are of the flexible type, having a basis weight of from about 5 to about 100 lbs. per ream of 2,880 square feet. These webs can be absorbent if desired. Preferably, the nonwoven fibrous sheets of this invention have a crepe ratio of from about 5 to about 50%, and most preferably of from about 5 to about 20%. The crepe ratio is calculated by the following formula:

$$\text{Crepe Ratio (\%)} = \frac{\text{(Crepe drum speed)} - \text{(wind-up reel speed)}}{\text{(wind-up reel speed)}} \times 100$$

Certain nonwoven sheets according to this invention have excellent flow rate characteristics to permit their use as a facing layer in disposable diapers, sanitary napkins and the like. Specifically, fluids, such as urine, will rapidly pass through such nonwoven sheets into an underlying absorbent pad or batt of the sanitary napkin or disposable diaper. The excellent flow rate characteristics through the sheet into the underlying absorbent pad are believed to be due to the low density, high bulk construction of said sheets in the regions which are free of the permanent binder. Moreover, the highly porous sheet regions tend to resist the reverse capillary flow of urine back through the facing sheet to wet a wearer of the diaper.

Other objects and advantages of this invention will become apparent upon reading the detailed description which follows, taken in conjunction with the drawings.

DESCRIPTION OF THE PREFERRED EMBODIMENT OF THE INVENTION

At the outset, it should be clearly understood that the method of the present invention may be employed to fabricate a wide variety of dry-formed sheets. For example, the dry-formed sheets can range in basis weight from about 5 to about 100 lbs. per ream of 2,880 square feet. Also the sheets can include various percentages of short cellulosic fibers of a papermaking length less than ¼ inch, and longer length fibers or filaments. The webs of this invention can be formed by air-laying, carding, garnetting and similar dry-forming techniques. The description which follows will be directed to the formation of dry-formed webs by carding, in which 100% of the fibers have a textile-length greater than ¼ inch, and generally up to about 3 inches.

Figure 1:
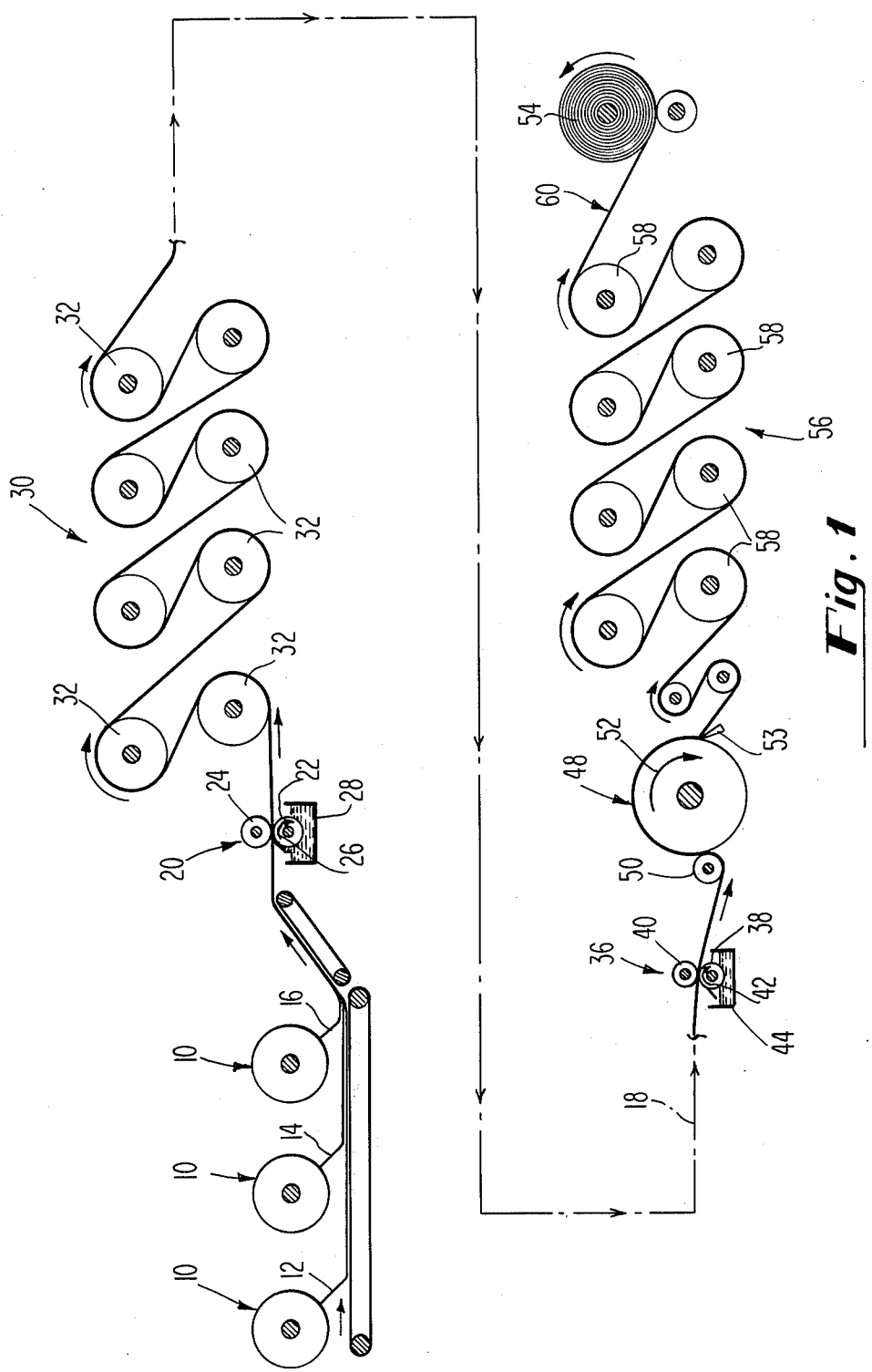
FIG. 1 is a schematic representation of the preferred method of this invention.

Referring to the process depicted in FIG. 1, a plurality of carding machines are schematically indicated at 10. These carding machines form a plurality of staple-length fibrous layers 12, 14 and 16 which are directed into overlying relationship with each other to form a low integrity fibrous web 18 having a basis weight of from about 5 to about 30 pounds per ream of 2,880 square feet. The web 18 can be formed by employing the specific method and apparatus disclosed in U.S. Pat.

No. 3,772,107, issued on Nov. 13, 1973, and assigned to Scott Paper Company. That patent is incorporated by reference into the instant application.

The web 18 is then directed through a temporary binder application station 20, which may be of a conventional padding type, to apply a large quantity of a temporary binder solution or dispersion to the web. The station 20 consists of a pair of rolls 22 and 24 which establish a bonding nip between them. The lower roll 22 may be a smooth, or rough surface padding roll which will carry a large quantity of fluid into the nip. This lower roll 22 is continuously rotated in the direction of arrow 26 through a vat 28 containing the temporary bonding material therein, and the outer surface of said roll carries the binder into engagement with a surface of the low integrity web 18 to impregnate said web. A suitable temporary binder is a 1½% solids, by weight, cooked pearl starch dispersion; and from about 100% to about 200% of the dispersion, by weight, based on the air-dry weight of the fibers in the web 18, is applied to said web. After the temporary binder has been applied to the web 18, said web is dried by directing it through a drying station 30 which consists of a plurality of dryer cans 32. At this point in the operation, a preferred temporarily bonded web 18 has a basis weight range of from approximately 8 to 14 lbs. per ream.

The temporarily bonded web 18 is directed from the dryer cans 32 through a permanent binder application station 36, which preferably is a gravure print station. The permanent binder application station 36 includes a lower roll 38 and an upper roll 40 which define a nip therebetween. The roll 38 is a conventional gravure roll having a plurality of binder-receiving cells formed in the outer surface thereof. The cells are arranged according to the desired spaced-apart binder pattern that is to be imparted to the web. This gravure roll 38 continuously rotates in the direction of arrow 42 through a vat 44 containing a permanent binder material therein. After passing through the vat, a doctor blade 46 removes excess binder from the roll surface 42 prior to the surface engaging the temporarily bonded web. The gravure printing roll 38 applies the permanent binder in a predetermined pattern to the surface of the web, preferably to cover an area of up to about 35% of its surface area. Preferably, from about 5 to about 30% solids add-on of permanent binder, based on the dry fiber weight of the web, is applied at station 36. Since the web 18 is relatively dry when it reaches the permanent bonding station 36, the permanent binder does not tend to migrate to any significant extent within the plane of the web to thereby adversely effect the porosity of said web in the regions between the areas containing said permanent binder. Preferably, the permanent binder is a self-cross-linking latex dispersion, such as for example, a copolymer of polyethylene and vinyl acetate sold under the trademark TR-120 by Air Products and Chemical Inc. of Allentown, Pa.

After the temporarily bonded web 18 has been printed with a permanent binder at station 36, it is conveyed to a creping drum 48 to which it is adhered by a pressure roll 50. In the preferred embodiment of this invention the creping drum is heated to remove moisture applied to the web 18 at the bonding station 36. The permanent binder provides the adhering force by which the web is held on the creping drum surface as the web is dried on said surface. Starting this another way, the printed web is adhered to the creping drum substantially only, or most tenaciously, in the regions of the web occupied by the permanent binder at the time the web is creped from the drum. The creping drum 48 is continuously rotated in the direction of arrow 52, and at a downstream end of said creping drum, the web is creped by a creping doctor blade 53. At this point in the operation, much of the moisture applied to the web at the permanent binder application station 36 has been removed; the web having a remaining moisture content of from about 3% to about 25%, and preferably about 7%. The speed ratio between the creping drum 48 and wind-up reel 54 is controlled to provide a crepe ratio in the machine-direction of from about 5 to about 25%. After creping, the web is passed through a setting station 56 which comprises a plurality of dryer cans 58. As the web passes through the setting station 56 the adhesive is maintained in a heated condition to further dry the web and to cure the binder for enhancing the wet tensile strength to complete the formation of nonwoven sheet 60 of this invention.

The creping of the web 18 is performed in a conventional way by the creping doctor blade 53. However, since the web 18 is only adhered to the creping drum 48 in a pattern having either a reticular form or comprising a plurality of spaced discrete areas, the creping doctor blade 53 causes the unbonded web portions, which are not tenaciously attached to the creping drum 48, to puff, or arch up to form a bulky, porous structure. The temporary bonds in the web 18 tend to initially resist the compressive action imposed upon said web by the creping doctor blade 53. However, when the force exceeds the compressive loading which can be tolerated by the temporary bonds it is believed that the temporary bonds will rupture in a relatively explosive manner to cause the web to become highly puffed in the regions which are free of permanent binder for achieving enhanced bulk and reduced density. Accordingly, the temporary brittle bonds are actually employed to enhance the bulking of the nonwoven web of this invention, and since these brittle bonds are broken or fractured by the creping operation, the brittleness, or stiffness imparted to the web by the temporary bonds is eliminated.

Applicant's invention is markedly different from the prior art processes for producing dry-formed nonwoven sheets having textile-like properties. Specifically, it has been taught in the prior art that when brittle bonds are present in an amount which can adversely affect the properties of the end product, these bonds are physically washed out by a liquid, such as water, after the nonwoven sheet has been formed. This additional step of washing out the brittle bonds requires a substantial quantity of water; thus requiring a subsequent drying operation to render the web usable. If applicant's invention, no washing is required to remove the brittle bonds. Moreover, applicant's process not only removes a significant number of the temporary brittle bonds, but actually takes advantage of the brittle property of the temporary bonds to achieve a high bulk, low density web construction. This unique method of forming a dry-formed nonwoven sheet is neither shown nor suggested by any of the prior art of which applicant has knowledge.

Figure 2:
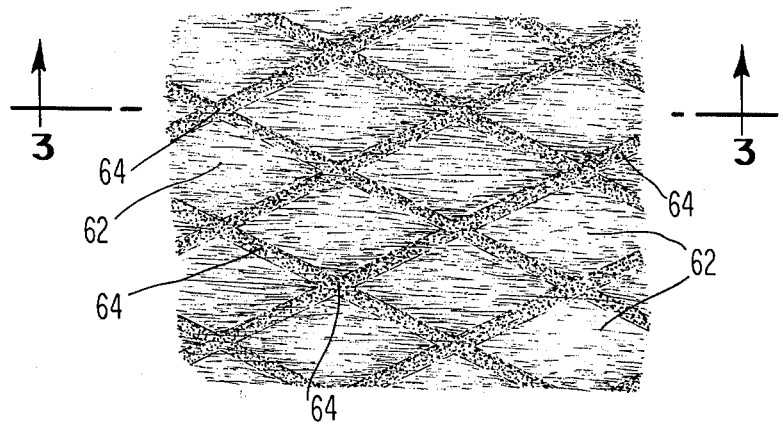
FIG. 2 is a plan view of a nonwoven sheet of this invention formed in accordance with the process steps depicted in FIG. 1.
Figure 3:
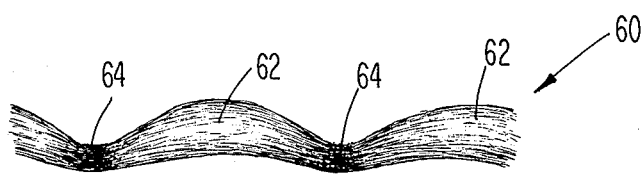
FIG. 3 is a sectional view along line 3—3 of FIG. 2, showing a somewhat idealized configuration of a nonwoven fibrous sheet formed in accordance with the process steps depicted in FIG. 1.

Referring to FIGS. 2 and 3, a creped, adhesively bonded, nonwoven fibrous sheet 60 according to this invention is formed from textile-length fibers having a length of approximately 1 9/16 inches. The adhesively bonded, creped sheet 60 has a basis weight of approximately 15 lbs./ream of 2,880 square feet, and the preferred basis weight range is from about 5 to about 30 lbs./ream. The sheet 60 has an undulating configuration imparted to it by the creping operation, and regions 62 disposed between the permanently bonded areas 64 of the sheet are puffed up into a high bulk, low density construction. The sheet 60 preferably has a crepe ratio of from 5 to about 25%. The particular configuration of the sheet 60 will vary, depending, at least in part, upon the particular pattern of the permanent binder. However, the regions 62 of the sheet which are free of permanent binder will be puffed up and of a lower density than these regions prior to creping.

The sheet 60 has been found to be highly desirable for use as a cover sheet in disposable diapers. Specifically, the nonwoven sheet 60 of this invention is highly porous, especially in the puffed up regions 62, to permit a rapid flow of urine through its thickness into an internal absorbent pad or batt of the disposable diaper. In view of the highly porous construction (i.e., large capillaries) of the sheet 60, and the greater capillary attraction for an underlying absorbent pad of the diaper, urine is not prone to wick laterally within the plane of the sheet, and accordingly, urine is not likely to wick to the side margins of the diaper and escape therefrom to damage outer garments of a wearer. Moreover, in the preferred embodiment of the invention the binder pattern 64 is disposed in a reticular, net-like pattern to completely surround regions 62 of the diaper which are free of permanent binder. The permanent binder, in its set condition, is preferably hydrophobic, and thereby the sheet regions 62 which are free of permanent binder are completely surrounded by hydrophobic boundaries which further impede the lateral flow of urine within the plane of the fabric.

The nonwoven sheet 60, because of its highly porous construction, resists the reverse capillary flow of urine back through the facing sheet which would wet a wearer of the diaper. Accordingly, the sheet 60 of this invention permits rapid flow or urine into an internal absorbent component of a diaper, and thereafter, resists the wetback of urine through the sheet to prevent the wetting of the wearer.

In the most preferred embodiment of this invention, the creped, adhesively bonded nonwoven sheet 60 is employed as the facing cover sheet in the one-piece, multilayer, disposable diapers disclosed and claimed in U.S. patent application Ser. No. 519,415, filed Oct. 31, 1974 now U.S. Pat. No. 3,916,900, issued Nov. 4, 1975, and assigned to Scott Paper Company. The subject matter of that application is incorporated into the instant application by reference.

Figure 4:
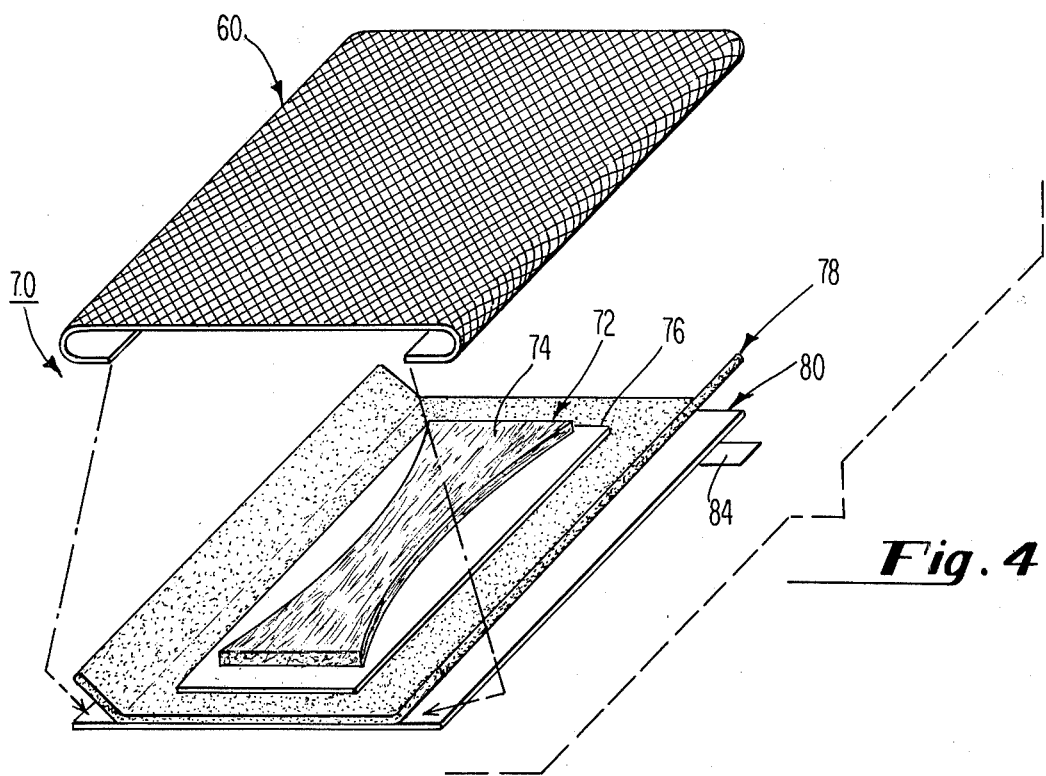
FIG. 4 is an exploded isometric view of a disposable diaper employing a nonwoven sheet of this invention.

Referring to FIG. 4, an exploded isometric view of one embodiment of a disposable diaper 70, which is disclosed in detail in application Ser. No. 519,415, includes the moisture-previous facing sheet 60; an absorbent core 72 including a loosely compacted fibrous batt 74, and a fibrous wicking layer 76 having a greater density than said fibrous batt; an elastomeric, wet-stable foam layer 78; and a moisture-impervious backing sheet 80. If desired, a pair of adhesive tape fasteners 82 (only one of which is shown in FIG. 4) can be included adjacent rear end margins of the diaper to secure said diaper about the body of a wearer.

It is understood that the nonwoven sheet 60 can be employed if any desired diaper structure; however, the preferred diaper structures are of the type which include an absorbent pad disposed between a moisture-previous facing layer and a moisture impervious backing layer.

As indicated earlier, many different techniques can be employed to form dry-formed webs which can be further processed in accordance with the method of this invention. Specifically, a dry-formed web can be formed from over 50%, by weight, short cellulosic fibers of a papermaking length less than ¼ inch. A preferred air-laid web construction includes from about 75 to about 95% short cellulosic fibers of a papermaking length less than ¼ inch; the remaining fiber composition being longer reinforcing fibers having a length greater than ¼ inch, and preferably greater than ¾ inch. The air-laid web can be formed by any well-known prior art technique; one of the most preferred techniques being disclosed in U.S. Pat. No. 3,862,472, issued on Jan. 28, 1975, and assigned to Scott Paper Company. This last mentioned patent is incorporated by reference into the instant application.

Having described my invention, I claim:

1. A method for forming a bulky, flexible, stretchable, nonwoven fibrous sheet, said method comprising the steps of:
  A. dry-forming a low integrity, fibrous web having a basis weight of from about 5 to about 100 lbs. per ream of 2,880 square feet;
  B. applying a temporary binder uniformly and continuously over the planar extent of a surface of the web;
  C. setting the binder to form brittle, fragile, interfiber bonds which establish sufficient web integrity for subsequent processing, said fragile bonds being brittle enough to be broken during a subsequent creping operation; thereafter
  D. applying a permanent binder to a surface of the web which is stabilized by said temporary binder, said permanent binder being applied in a solids weight percent of from about 5 to about 30, based on the dry weight of the temporarily bonded web, said permanent binder being applied in a spaced-apart pattern covering from about 5 to about 60% of the surface area of the web and extending at least 10% through the thickness of said web;
  E. adhering to a creping surface, by use of the permanent binder, the areas of a surface of the web in which the permanent binder has been applied;
  F. creping said web from the creping surface for breaking temporary brittle bonds in said web to enhance the bulk, flexibility and extensibility characteristics of said web; and
  G. setting said permanent binder to complete the formation of the nonwoven sheet which is stabilized by said permanent binder.

2. The method according to claim 1, wherein said permanent binder is applied to the surface of said web in a spaced-apart pattern covering no more than about 35% of the area of said surface.

3. The method according to claim 2, including applying the permanent binder in an interconnected, reticular pattern to define a discontinuous, intermittent pattern of discrete areas that are free of permanent binder, said discrete areas including temporary brittle bonds therein prior to the creping step said creping step foreshortening the machine dimension of said web and breaking the brittle bonds in the discrete areas.

4. The method according to claim 2, including forming said sheet with a basis weight of from about 5 lbs. to about 30 lbs. per ream of 2,880 square feet.

5. The method according to claim 4, including forming the web of over 50% stable-length fibers having a length in excess of ¼ inch.

6. The method according to claim 5, including forming the web from 100% stable fibers having a length in excess of ¼ inch.

7. The method according to claim 6, including forming said web with the fibers predominantly aligned substantially in the machine-direction of web formation.

8. The method according to claim 5, wherein the creping of the web establishes a crepe ratio in the sheet of from about 5 to about 50% in the machine direction.

9. The method according to claim 8, wherein the creping of the web establishes a crepe ratio in the sheet of from about 10 to about 20%, in the machine direction.

10. The method according to claim 1, wherein said web is formed in a dry condition by conveying substantially individualized fibers in a gaseous medium onto a foraminous surface upon which the fibers are deposited in web form, and through which the gaseous medium passes.

11. The method according to claim 10, wherein said web is formed in a dry condition from over 50% short cellulosic fibers of a papermaking length less than ¼ inch.

12. The method according to claim 10, wherein said web is formed in a dry condition from a blend of substantially individualized fibers of a papermaking length less than ¼ inch and substantially individualized staple-length fibers in excess of ¼ inch.

13. The nonwoven sheet made according to the method of claim 1.

14. The nonwoven sheet made according to the method of claim 2.

15. The nonwoven sheet made according to the method of claim 3.

16. The nonwoven sheet made according to the method of claim 4.

17. The nonwoven sheet made according to the method of claim 5.

18. The nonwoven sheet made according to the method of claim 6.

19. The nonwoven sheet made according to the method of claim 7.

20. The nonwoven sheet made according to the method of claim 8.

21. The nonwoven sheet made according to the method of claim 9.

22. The nonwoven sheet made according to the method of claim 11.

23. The method according to claim 1, wherein the temporary binder is applied so that it completely penetrates through the thickness of the web.

24. The method according to claim 23, including forming said sheet with a basis weight of from about 5 lbs. to about 30 lbs. per ream of 2,880 square feet.

* * * * *